United States Patent
Higuchi

(10) Patent No.: US 12,226,463 B2
(45) Date of Patent: *Feb. 18, 2025

(54) PHARMACEUTICAL COMPOSITION, PACKAGE AND METHOD FOR PRODUCING THE SAME

(71) Applicant: SEIKAGAKU CORPORATION, Tokyo (JP)

(72) Inventor: Mine Higuchi, Tokyo (JP)

(73) Assignee: SEIKAGAKU CORPORATION, Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 18/133,168

(22) Filed: Apr. 11, 2023

(65) Prior Publication Data

US 2023/0263871 A1 Aug. 24, 2023

Related U.S. Application Data

(63) Continuation of application No. 16/975,546, filed as application No. PCT/JP2019/007437 on Feb. 27, 2019, now Pat. No. 11,648,299.

(30) Foreign Application Priority Data

Feb. 28, 2018 (JP) .................................. 2018-035884

(51) Int. Cl.
A61K 38/51 (2006.01)
A61K 9/19 (2006.01)

(52) U.S. Cl.
CPC ................ *A61K 38/51* (2013.01); *A61K 9/19* (2013.01); *C12Y 402/02004* (2013.01)

(58) Field of Classification Search
CPC ... C12Y 402/02004; A61K 9/19; A61K 38/51
See application file for complete search history.

(56) References Cited

U.S. PATENT DOCUMENTS

| | | |
|---|---|---|
| 5,496,718 A | 3/1996 | Hashimoto et al. |
| 6,001,630 A | 12/1999 | Ichikawa et al. |
| 2010/0168011 A1 | 7/2010 | Jennings, Jr. et al. |
| 2013/0230509 A1 | 9/2013 | Matsuyama et al. |
| 2013/0266555 A1 | 10/2013 | Sirogane et al. |
| 2015/0136723 A1 | 5/2015 | Bamba et al. |

FOREIGN PATENT DOCUMENTS

| | | | |
|---|---|---|---|
| EP | 0 875 253 A2 | 11/1998 | |
| JP | H6-135851 A | 5/1994 | |
| JP | H6-153947 A | 6/1994 | |
| JP | H7-67642 A | 3/1995 | |
| JP | 110236336 * | 8/1999 | ............. A61K 38/51 |
| JP | H11-236336 A | 8/1999 | |
| JP | 2008-50320 A | 3/2008 | |
| JP | 2010-512399 A | 4/2010 | |
| WO | WO 2005/046699 A1 | 5/2005 | |
| WO | WO 2012/081227 A1 | 6/2012 | |
| WO | WO 2013/179514 A1 | 12/2013 | |

OTHER PUBLICATIONS

Yamagata, T., "Purification and Properties of Bacterial Chondroitinases and Chondrosulfatases", The Journal of Biological Chemistry, vol. 243, No. 7, p. 1523-1535. (Year: 1968).*
ISR for PCT/JP2019/007437, dated Apr. 9, 2019 (w/ translation).
IPRP for PCT/JP2019/007437, dated Sep. 1, 2020 (w/ translation).

* cited by examiner

*Primary Examiner* — Michelle F. Paguio Frising
*Assistant Examiner* — Grant C Currens
(74) *Attorney, Agent, or Firm* — GREENBLUM & BERNSTEIN, P.L.C.

(57) ABSTRACT

A pharmaceutical composition containing a lyophilized saccharide-degrading enzyme having excellent titer, and a package containing the pharmaceutical composition. The pharmaceutical composition is a unit dose formulation containing a lyophilized saccharide-degrading enzyme with a titer of not less than 0.3 unit/μg as an active ingredient, and contains the saccharide-degrading enzyme in an amount of not less than 2 μg and not more than 6 μg.

17 Claims, No Drawings

PHARMACEUTICAL COMPOSITION, PACKAGE AND METHOD FOR PRODUCING THE SAME

This is a Continuation of U.S. application Ser. No. 16/975,546, which is a U.S. National Stage entry of PCT/JP2019/007437, filed Feb. 27, 2019, which claims priority to JP App. No. 2018-035884, filed Feb. 28, 2018. The disclosure of each of the applications identified above is herein incorporated by reference in its entirety.

TECHNICAL FIELD

The present invention relates to a pharmaceutical composition that includes a saccharide-degrading enzyme as an active ingredient, to a package comprising the composition contained in a container, and to a method for producing the same.

BACKGROUND ART

Pharmaceutical compositions that comprise saccharide-degrading enzymes as active ingredients are used in various disease fields. For example, pharmaceutical compositions for treatment of lysosomal disease such as Aldurazyme®, Elaprase®, Naglazyme®, Replagal® and Vimizim®, wherein the active ingredients are saccharide-degrading enzymes at about 3 mg/vial to about 10 mg/vial, are marketed as liquid preparations for injection. Also, International Publication No. WO 2012/081227, for example, describes a therapeutic agent for disc herniation containing a saccharide-degrading enzyme (particularly chondroitinase ABC) as the active ingredient.

SUMMARY OF INVENTION

Lyophilized preparations are superior to liquid preparations from the viewpoint of reducing distribution cost. On the other hand, titers of enzyme are often significantly reduced due to lyophilization, and even more so if the enzyme is in a trace amount, and for this reason, some ideas have been introduced in production of lyophilized preparations so as to allow products with the desired enzyme activity to be obtained. For example, the Examples of International Publication No. WO 2012/081227 describe an example in which, considering the drastic reduction in titer resulting from lyophilization, a lyophilized preparation is obtained by lyophilization after the enzyme in a large excess of the number of units necessary for a single dose has been put into a container. As described in this publication, once the obtained lyophilized preparation has been dissolved and diluted, it is separated off in the amount required for administration to prepare a dosing solution containing the active component in an amount necessary for a single dose.

In a method wherein a lyophilized preparation in an amount largely exceeding the unit dose is prepared first and then a portion is separated off as a single dose, a large remaining amount of enzyme that is not used for administration is discarded. So, there have been cases where large remaining amounts of expensive enzyme are wasted.

Therefore, one object of one aspect of the present invention is to provide a pharmaceutical composition containing a saccharide-degrading enzyme as an active ingredient, wherein reduction in titer resulting from preparation by lyophilization is suppressed.

As a result of much ardent research by the present inventor in light of the problem mentioned above, a means was found for providing a pharmaceutical composition containing a saccharide-degrading enzyme with suppressed reduction in titer before and after lyophilization, and the present invention was thus completed.

One aspect of the present invention relates to a pharmaceutical composition that is a unit dose formulation containing a lyophilized saccharide-degrading enzyme with a titer of not less than 0.3 unit/μg as an active ingredient, and containing the enzyme in an amount of not less than 2 μg and not more than 8 μg.

Another aspect of the present invention relates to a method for producing a package comprising a pharmaceutical composition and a container containing the pharmaceutical composition, wherein the method comprising a step of putting a solution comprising not less than 2 μg and not more than 8 μg of a saccharide-degrading enzyme into the container, and a step of lyophilizing the solution so that a unit dose of the pharmaceutical composition can be provided.

DESCRIPTION OF EMBODIMENTS

According to one aspect of the present invention, it is possible to provide a pharmaceutical composition containing a lyophilized saccharide-degrading enzyme, wherein reduction in titer by the lyophilization is greatly suppressed.

The present invention will now be described in detail, with the understanding that the present invention is not limited by the embodiments described. As used herein, the term "step" refers not only to an independent step, but also includes any step that cannot be clearly distinguished from other steps, if the initial purpose of the step is achieved. When multiple substances corresponding to each component are present in the composition, the content of each component in the composition means the total of the multiple substances in the composition, unless otherwise specified.

(1) Pharmaceutical Composition and Package

The pharmaceutical composition is a lyophilized preparation containing a saccharide-degrading enzyme as an active ingredient. The pharmaceutical composition is a unit dose formulation containing a lyophilized saccharide-degrading enzyme with a titer of not less than 0.3 unit/μg as an active ingredient, and containing the saccharide-degrading enzyme in an amount of not less than 2 μg and not more than 8 μg. As used herein, "unit dose" means the necessary amount prepared for a single administration, a unit dose formulation being formulated with the pharmaceutical composition in the unit dose. The unit dose may include an added amount necessary for preparation of a single dosing solution, in addition to the effective dose.

In this pharmaceutical composition, reduction in the titer of saccharide-degrading enzyme due to lyophilization is greatly suppressed. Reduction in titer due to storage is also greatly suppressed. Furthermore, since the pharmaceutical composition is a lyophilized preparation that is prepared in advance to each unit dose, it is also superior from the viewpoint of convenience, hygiene, safety, etc., in a medical setting.

The package comprises at least a container and a pharmaceutical composition contained in the container, and it therefore has the pharmaceutical composition contained in the container.

The "saccharide-degrading enzyme" is not particularly limited, as long as it is one that can be used as a drug. Examples of saccharide-degrading enzymes can include, for example, glycosaminoglycan degrading enzymes; glycosidase; peptides: N-glycanase (PNGaseF, endoglycosidase H, etc.), α-L-iduronidase, α-galactosidase, β-galactosidase, β-glucuronidase, β-glucocerebrosidase, idursulfase, iduronate-2-sulfatase, N-acetylgalactosamine-6-sulfatase, N-acetylgalactosamine-4-sulfatase, etc. Examples of glycosaminoglycan degrading enzymes include, for example, keratanases such as keratanase I and keratanase II; heparinases such as heparinase I, heparinase II and heparinase III; heparitinases such as heparitinase IV, heparitinase V, heparitinase T-I, heparitinase T-II, heparitinase T-III and heparitinase T-IV; chondroitinases such as chondroitinase ABC, chondroitinase ACI, chondroitinase ACII, chondroitinase ACIII, chondroitinase B and chondroitinase C; hyaluronidases such as hyaluronidase derived from Actinomycetes and hyaluronidase derived from *Streptococcus*, etc. Examples of glycosidases include, for example, microbial β-galactosidase, α-galactosidase, etc.

In one embodiment, a glycosaminoglycan degrading enzyme is used as the saccharide-degrading enzyme. Glycosaminoglycan degrading enzymes include hyaluronidases, chondroitinases, heparinases, keratanases, heparanases, heparitinases, etc. Chondroitinases are preferred saccharide-degrading enzymes, among which chondroitinase ABC, chondroitinase B, chondroitinase ACI and chondroitinase ACII are more preferred, and chondroitinase ABC is especially preferred. Chondroitinase ABC may also be Condoliase.

There are no particular restrictions on the source of the saccharide-degrading enzyme. In one preferred embodiment, a microbial saccharide-degrading enzyme is used. For example, non-restrictive examples of microbes include those belonging to *Bacillus, Escherichia, Pseudomonas, Flavobacterium, Proteus, Arthrobacter, Streptococcus, Bacteroides, Aspergillus, Elizabethkingia, Streptomyces*, etc.

When the saccharide-degrading enzyme is chondroitinase ABC, for example, an example can be one derived from *Proteus vulgaris* (for example, *Proteus vulgaris* chondroitinase ABC).

The method for producing the saccharide-degrading enzyme, etc., is not particularly restricted. An exemplary method for producing the saccharide-degrading enzyme includes a step of obtaining a culture of microbes or animal cells that produce the saccharide-degrading enzyme, and a step of collecting the saccharide-degrading enzyme from the cultured product.

The saccharide-degrading enzyme produced by the microbes may be the original product of the microbes, or it may be obtained after modifying the microbes by a genetic engineering method, etc., as described below, so as to produce the target enzyme. For example, when the saccharide-degrading enzyme is chondroitinase ABC, it may be produced by culturing a microbe such as *Proteus vulgaris*, or it may be produced by a genetic engineering method using DNA coding for the chondroitinase ABC, etc. The saccharide-degrading enzyme may have the same amino acid sequence as the original product of the organism, but alternatively it may have a deletion, substitution and/or addition, etc., of some of the amino acids, as long as the intended object of the drug is still achieved.

Examples of microbes can include, for example, microbes belonging to *Bacillus, Escherichia, Pseudomonas, Flavobacterium, Proteus, Arthrobacter, Streptococcus, Bacteroides, Aspergillus, Elizabethkingia* and *Streptomyces*. The growth conditions (for example, culture medium, culturing conditions, etc.) for the microbe can be set as desired by a person skilled in the art, being appropriately selected according to the microbe used. By using a microbe to produce the saccharide-degrading enzyme, it is possible to produce larger amounts at lower cost than by production of the saccharide-degrading enzyme using animal cells.

The method for producing the saccharide-degrading enzyme may include a step of introducing a recombinant vector that expresses a gene coding for the target saccharide-degrading enzyme, into a host. The vector used can be, for example, a suitable expression vector (phage vector, plasmid vector or the like) (preferably including a regulatory sequence such as a promoter), that is able to express the introduced gene. The vector is selected as appropriate for the host cells. More specifically, examples of these host-vector systems include combinations of *Escherichia coli* (*E. coli*) with prokaryotic cell expression vectors such as the pET Series, pTrcHis, pGEX, pTrc99, pKK233-2, pEZZ18, pBAD, pRSET and pSE420; or combinations of mammalian cells such as COS-7 cells or HEK293 cells with mammalian cell expression vectors such as the pCMV Series, pME18S Series or pSVL; as well as insect cells, yeast and *Bacillus subtilis* host cells, etc., and their various corresponding vectors.

Also, as above-described vectors, it is possible to use the vectors that are constructed so as to express fusion proteins of the proteins encoded by the transferred genes, with marker peptides or signal peptides. Examples of such peptides include, for example, Protein A, the insulin signal sequence, His, FLAG, CBP (calmodulin-binding protein), GST (glutathione-S-transferase), etc. Regardless of the vector used, a common method may be used for treatment with restriction enzymes, etc., that allow subsequent linkage of the nucleic acid sequence insert and vector, the linkage being after blunting or with sticky ends, as necessary.

Transformation of the host with the vector can be carried out by a common method. For example, the vector can be introduced into the host for transformation, by a method using a commercially available transfection reagent, or by a DEAE-dextran method, electroporation method, or a method using a gene gun, etc.

The growth conditions (culture medium, culturing conditions, etc.) for the microbes or animal cells that produce the saccharide-degrading enzyme are selected as appropriate for the microbes or cells used. In the case of where *E. coli* is used, for example, a culture medium appropriately prepared with LB medium, etc., as the main component can be used. Also, for example, when COS-7 cells are used as the host cells, DMEM medium containing about 2% (v/v) fetal bovine serum can be used for culturing under a condition of 37° C.

The saccharide-degrading enzyme can be collected from the growth product by known methods for extraction and purification of proteins, depending on the form of the saccharide-degrading enzyme that is produced. For example, when the saccharide-degrading enzyme is produced in soluble form secreted in the medium (the culture supernatant), the medium may be harvested and used directly as the saccharide-degrading enzyme. When the saccharide-degrading enzyme is produced in soluble form secreted into the cytoplasm, or in an insoluble (membrane-bound) form, it can be extracted by a treatment procedure such as extraction by cell disruption, such as a method using a nitrogen cavitation device, homogenization, a glass bead mill method, sonication, an osmotic shock method or a freezing-thawing method, or surfactant extraction, or a combination of these methods. The saccharide-degrading enzyme may also be purified by conventional and publicly known processes of the prior art such as salting out, ammonium sulfate fractionation, centrifugal separation, dialysis, ultrafiltration, adsorption chromatography, ion-exchange chromatography, hydrophobic chromatography, reversed-phase chromatography, gel permeation chromatography, affinity chromatography or electrophoresis, or a combination of these processes, etc.

The saccharide-degrading enzyme may be used alone or as a combination of two or more different types. The saccharide-degrading enzyme may also have addition of chemically modified groups that are publicly known in the prior art, such as by acetylation, polyalkylene glycolation (for example, polyethylene glycolation), alkylation, acylation, biotinylation, labeling (for example, labeling with a fluorescent substance, a luminescent substance, etc.), phosphorylation or sulfation.

The pharmaceutical composition may include a pharmaceutically acceptable carrier. As used herein, a "pharmaceutically acceptable carrier" is typically a component normally used in drugs, such as a commonly used excipient, binder, buffering agent, water for injection, tonicity agent, preservative or soothing agent.

Examples of buffering agents include, for example, buffering agents containing one or more from among hydrochloric acid, sodium hydroxide, sodium carbonate, sodium hydrogencarbonate, phosphoric acid, potassium dihydrogenphosphate, dipotassium hydrogenphosphate, sodium dihydrogenphosphate, disodium hydrogenphosphate, aminoacetic acid, sodium benzoate, citric acid, sodium citrate, acetic acid, sodium acetate, tartaric acid, sodium tartrate, lactic acid, sodium lactate, ethanolamine, arginine, ethylenediamine, etc., with sodium dihydrogenphosphate and disodium hydrogenphosphate being preferred.

Examples of tonicity agents include sodium chloride, potassium chloride, glycerin, mannitol, sorbitol, boric acid, borax, glucose, propylene glycol, etc.

For example, specific examples of other pharmaceutically acceptable carriers include dextrans, sucrose, lactose, maltose, xylose, trehalose, mannitol, xylitol, sorbitol, inositol, serum albumin, gelatin, creatinine, polyalkylene glycol, nonionic surfactants (for example, polyoxyethylene sorbitan fatty acid ester, polyoxyethylene hydrogenated castor oil, sucrose fatty acid ester and polyoxyethylene-polyoxypropylene glycol), etc., among which sucrose and/or polyalkylene glycol are preferred, and sucrose and/or polyethylene glycol are more preferred. Polyethylene glycol preferably has an average molecular weight of not less than 200 and not more than 25000, and more preferably it is a solid at ordinary temperature, for example, with an average molecular weight of not less than 2000 and not more than 9000, and even more preferably not less than 3000 and not more than 4000. Examples of polyethylene glycol can include, for example, polyethylene glycol with an average molecular weight of 3250, 3350 and 4000. When a mixture of polyethylene glycol and sucrose is used as the pharmaceutically acceptable carrier, they are preferably mixed such that the weight ratio of polyethylene glycol/sucrose is usually in the range of 1/10 to 10/1, and more preferably such that the weight ratio of polyethylene glycol/sucrose is about 2/1.

As used herein, the "container" is not particularly restricted as long as it is able to contain the pharmaceutical composition. Examples of containers include syringes, vials, ampules, injectors, etc., with vials being preferred. The material of the container can be glass, plastic, etc., for example, with glass being preferred. Glass includes borosilicate glass, soda lime glass, etc., for example. The container preferably also has a stopper member or cap, and more preferably it has a rubber stopper. There are no particular restrictions on the size of the container, which may be not less than 0.5 mL and not more than 100 mL, for example, preferably not less than 1 mL and not more than 10 mL, more preferably not less than 2 mL and not more than 4 mL, and even more preferably 3 mL. The package comprising the pharmaceutical composition contained in the container may encapsulate an inert gas such as nitrogen gas or argon gas, or it may be deaerated.

The water content of the lyophilized preparation may be not more than 5% (w/w), for example, preferably not more than 3% (w/w), and more preferably not more than 2% (w/w). The "water content," as used herein, is the value measured by a coulometric titration method.

The present invention is characterized in that the amount of saccharide-degrading enzyme per unit dose of the pharmaceutical composition is not less than 2 µg and not more than 8 µg. While a smaller abundance of enzyme generally corresponds to more notable reduction in titer before and after lyophilization, the present inventors found, surprisingly, that limiting the amount of saccharide-degrading enzyme per unit dose of the pharmaceutical composition to the range of not less than 2 µg and not more than 8 µg can significantly suppress titer reduction before and after lyophilization. In a preferred embodiment, from the viewpoint of the effect of suppressing titer reduction before and after lyophilization, the amount of saccharide-degrading enzyme per unit dose of the pharmaceutical composition is not less than 2 µg and not more than 7 µg, not less than 2 µg and not more than 6 µg, or not less than 2.5 µg and not more than 6 µg. In a more preferred embodiment, the amount of saccharide-degrading enzyme per unit dose of the pharmaceutical composition is not less than 2 µg and not more than 5 µg, or not less than 2.5 µg and not more than 5 µg. In a particularly preferred embodiment, the amount of saccharide-degrading enzyme per unit dose of the pharmaceutical composition is not less than 3 µg and not more than 5 µg.

In a preferred embodiment, the amount of saccharide-degrading enzyme contained per container is not less than 2 µg and not more than 8 µg. In a more preferred embodiment, the amount of saccharide-degrading enzyme contained per container is not less than 2 µg and not more than 7 µg, not less than 2 µg and not more than 6 µg, or not less than 2.5 µg and not more than 6 µg. In an even more preferred embodiment, the amount of saccharide-degrading enzyme contained per container is not less than 2 µg and not more than 5 µg, or not less than 2.5 µg and not more than 5 µg. In a particularly preferred embodiment, the amount of saccharide-degrading enzyme contained per container is not less than 3 µg and not more than 5 µg.

The term "titer" means the enzyme activity (units) per 1 µg of saccharide-degrading enzyme, and it is expressed in a unit of unit/µg. In the present invention, the titer of the lyophilized saccharide-degrading enzyme is not less than 0.3 (unit/µg). In one embodiment, the titer of the lyophilized saccharide-degrading enzyme is not less than 0.3 (unit/µg) and not more than 1 (unit/µg). In another embodiment, the titer of the lyophilized saccharide-degrading enzyme is not less than 0.32 (unit/µg) and not more than 1 (unit/µg). In a more preferred another embodiment, the titer of the lyophilized saccharide-degrading enzyme is not less than 0.34 (unit/µg) and not more than 1 (unit/µg). In an even more preferred another embodiment, the titer of the lyophilized saccharide-degrading enzyme is not less than 0.36 (unit/µg) and not more than 1 (unit/µg). In a particularly preferred another embodiment, the titer of the lyophilized saccharide-degrading enzyme is not less than 0.38 (unit/µg) and not more than 1 (unit/µg).

In one embodiment, the titer of the lyophilized saccharide-degrading enzyme is not less than 0.3 (unit/µg) and not more than 0.5 (unit/μg). In another embodiment, the titer of the lyophilized saccharide-degrading enzyme is not less than 0.36 (unit/μg) and not more than 0.5 (unit/μg).

The "unit (U)" indicates the activity of the saccharide-degrading enzyme, with 1 U being the amount that frees the equivalent of 1 micromole of decomposition product from substrate per unit time, under optimum temperature and optimum pH conditions. For example, when the saccharide-degrading enzyme is chondroitinase ABC, 1 unit is the amount that frees 1 micromole of the unsaturated disaccharide per minute from sodium chondroitin sulfate (sodium chondroitin sulfate conforming to the Japanese Pharmaceutical Codex 2002), under conditions of pH 8.0, 37° C.

In one embodiment, the enzyme activity (saccharide-degrading enzyme activity) per unit dose is not less than 4 units, for example. In another embodiment, the enzyme activity per unit dose is not less than 0.1 unit and not more than 4 units, for example. In a preferred embodiment, the enzyme activity per unit dose is not less than 0.5 units and not more than 3 units. In a more preferred embodiment, the enzyme activity per unit dose is not less than 0.9 units and not more than 3 units, or not less than 0.9 units and not more than 2.5 units. In yet another preferred embodiment, the enzyme activity per unit dose is not less than 0.9 units and not more than 2 units, not less than 1.25 units and not more than 2 units, or 1.5 units.

In one embodiment, the enzyme activity per container is not more than 4 units, for example. In another embodiment, the enzyme activity per container is not less than 0.1 unit and not more than 4 units, for example. In a preferred embodiment, the enzyme activity per container is not less than 0.5 units and not more than 3 units. In a more preferred embodiment, the enzyme activity per container is not less than 0.9 units and not more than 3 units, or not less than 0.9 units and not more than 2.5 units. In yet another preferred embodiment, the enzyme activity per container is not less than 0.9 units and not more than 2 units, or not less than 1.25 units and not more than 2 units (for example, 1.5 units).

According to the present invention, a pharmaceutical composition in the form of a lyophilized unit dose formulation containing a small amount of saccharide-degrading enzyme (not less than 2 μg and not more than 8 μg) at a high titer (not less than 0.3 unit/μg) is provided.

The enzyme activity of the saccharide-degrading enzyme contained in the pharmaceutical composition in the form of a lyophilized preparation may be, for example, not less than 75%, preferably not less than 80%, more preferably not less than 85%, and even more preferably not less than 90%, where the enzyme activity before lyophilization is defined as 100%. A value of 100% means that the enzyme activity is the same before and after lyophilization.

According to one embodiment of the present invention, it is possible to provide a pharmaceutical composition having storage stability for a duration of 12 months or longer, for example. In a preferred embodiment, the pharmaceutical composition has a storage stability for a duration of 24 months or longer, and in a more preferred embodiment, the pharmaceutical composition has a storage stability for a duration of 36 months or longer. Although the upper limit for the storage stability is not particularly limited, it may be 48 months or shorter (such as 36 months or shorter), for example.

Here, the phrase "has a storage stability" means that the titer (%) after light-resistant storage under prescribed conditions (for example, 12 months or longer at 5° C.±3° C., 6 months or longer at 25° C.±2° C., or 3 months or longer or 6 months or longer at 40° C.±2° C.) is maintained to a pharmaceutically acceptable level. The "storage stability" herein is evaluated as the titer retention rate (%), for example. For example, the titer retention rate after Light-resistant storage of the sample for 12 months or longer at 5° C.±3° C. is, for example, not less than 90%, and preferably not less than 95%. The titer retention rate after Light-resistant storage of the sample for 24 months or longer at 5° C.±3° C. is, for example, not less than 90%, and preferably not less than 95%. The titer retention rate after Light-resistant storage of the sample for 36 months or longer at 5° C.±3° C. is, for example, not less than 90%, and preferably not less than 95%. The titer retention rate after Light-resistant storage of the sample for 6 months or longer at 25° C.±2° C. is, for example, not less than 90%, and preferably not less than 95%. The titer retention rate after Light-resistant storage of the sample for 3 months or longer at 40° C.±2° C. is, for example, not less than 90%, and preferably not less than 95%. The titer retention rate after storage of the sample for 6 months or longer at 40° C.±2° C. is, for example, not less than 65%, preferably not less than 70%, and more preferably not less than 75%. The term "titer retention rate (%)" means the value of the titer (%) after Light-resistant storage of the pharmaceutical composition or package of the present invention under conditions with a prescribed temperature (5° C.±3° C., 25° C.±2° C. or 40° C.±2° C.), calculated against 100% as the titer at the start of storage. A value of 100% means that the enzyme activity is the same at and after the start of storage.

According to one embodiment of the present invention, it is possible to provide a pharmaceutical composition having a shelf life of 12 months or longer. In a preferred embodiment, the pharmaceutical composition has a shelf life of 24 months or longer, and in a more preferred embodiment, the pharmaceutical composition has a shelf life of 36 months or longer. Although the upper limit for the shelf life is not particularly restricted, it may be 48 months or shorter (such as 36 months or shorter), for example.

As used herein, the "shelf life" means the period during which a drug can be expected to exhibit the same efficacy from the time when the drug has been confirmed to exhibit that efficacy, after subsequent storage by a specific storage method (for example, being Light-resistant at 5° C.±3° C., Light-resistant at 25° C.±2° C., or Light-resistant at 40° C.±2° C.).

References to the pharmaceutical composition herein may include the "pharmaceutical compositions contained in the container." The pharmaceutical composition contained in the container includes a unit dose of the saccharide-degrading enzyme.

The use of the pharmaceutical composition as described herein may be selected from among various known uses for saccharide-degrading enzymes. For example, examples of uses of pharmaceutical compositions containing saccharide-degrading enzymes as active ingredients can include, but are not particularly limited to, treatment for hernia, lysosomal disease, keloids, hypertrophic scars, muscular dystrophy and spinal cord injury. In a preferred embodiment, the pharmaceutical composition is used for treatment of hernia. In a more preferred embodiment, it is used for treatment of disc herniation (for example, lumbar disc herniation).

As used herein, "treatment" includes not only complete curing, but also amelioration of all or some of the symptoms of a disease, and suppression (including maintenance and slowed progression) of progression or prevention of a disease. Here, prevention includes preventing onset of symptoms associated with a disease, when the symptoms are not being exhibited. Prevention also includes, for example, preventing onset of organic lesions or suppressing development of symptoms not yet manifested, when symptoms associated with a disease are present even if no clear organic lesions are apparent.

The terms "as an active ingredient" and "effective dose," as used herein, mean an amount of ingredient suited for a reasonable risk/benefit ratio, and sufficient to obtain the desired response without excessive harmful side-effects (toxicity, irritation, etc.). The terms "as an active ingredient" and "effective dose" may vary depending on various factors such as the symptoms, physical constitution, age and sex of the patient to be treated. However, a person skilled in the art can determine the effective dose based on the results of one or more specific test examples in combination with common general technical knowledge, without having to conduct a separate test for each combination of the various factors.

As used herein, "patient" means an animal, and preferably a mammal (for example, a human, mouse, rat, hamster, guinea pig, rabbit, dog, cat, horse, etc.), and more preferably a human.

In a preferred embodiment, the pharmaceutical composition contained in the container is provided in a sterile state. There are no particular restrictions on the sterilization method for the pharmaceutical composition, and sterilization may be performed in any method known in the prior art, such as filtration sterilization or dry heat sterilization.

The form of administration of the pharmaceutical composition is also not particularly restricted and may be selected as appropriate for the disease to be treated, the symptoms, the severity, the patient attributes (for example, age, etc.), etc. The lyophilized preparation may be used as a solution in any desired solvent (for example, water for injection, physiological saline, etc.). The form of administration may be any route of administration, for example, such as intradiscal injection, intravenous injection, intramuscular injection, hypodermic injection or drip infusion. The dose of the pharmaceutical composition can also be appropriately set by a person skilled in the art according to the disease to be treated, the symptoms, the severity, the patient attributes (for example, age, etc.), etc.

Preferred specific modes of the present invention will now be described by way of example, with the understanding that they are not intended to limit the technical scope of the present invention. A pharmaceutical composition for treatment disc herniation may be explained as an example, as follows. But it is natural that the use of pharmaceutical compositions may not be limited.

(Pharmaceutical Composition 1)
  Active ingredient: Chondroitinase ABC
  Amount of enzyme per unit dose: not less than 2 μg and not more than 7 μg
  Enzyme titer: not less than 0.36 (unit/μg) and not more than 1 (unit/μg)
  Enzyme activity per unit dose: not less than 0.9 units and not more than 3 units
  Application: Disc herniation
(Pharmaceutical Composition 2)
  Active ingredient: Chondroitinase ABC
  Amount of enzyme per unit dose: not less than 2 μg and not more than 5 μg
  Enzyme titer: not less than 0.36 (unit/μg) and not more than 0.5 (unit/μg)
  Enzyme activity per unit dose: not less than 0.9 units and not more than 2.5 units
  Application: Disc herniation
(Pharmaceutical Composition 3)
  Active ingredient: Chondroitinase ABC
  Amount of enzyme per unit dose: not less than 2 μg and not more than 5 μg
  Enzyme titer: not less than 0.36 (unit/μg) and not more than 0.5 (unit/μg)
  Enzyme activity per unit dose: not less than 0.9 units and not more than 2 units
  Application: Disc herniation
(Pharmaceutical Composition 4)
  Active ingredient: Chondroitinase ABC
  Amount of enzyme per unit dose: not less than 2 μg and not more than 5 μg
  Enzyme titer: not less than 0.36 (unit/μg) and not more than 0.5 (unit/μg)
  Enzyme activity per unit dose: not less than 1.25 units and not more than 2 units
  Application: Disc herniation
(Pharmaceutical Composition 5)
  Active ingredient: Chondroitinase ABC
  Amount of enzyme per unit dose: not less than 3 μg and not more than 5 μg
  Enzyme titer: not less than 0.36 (unit/μg) and not more than 0.5 (unit/μg)
  Enzyme activity per unit dose: 1.5 units
  Application: Disc herniation (2) Kit In one embodiment, there is provided a kit containing a package comprising the pharmaceutical composition contained in a container, and a package insert or label explaining the use of the pharmaceutical composition for treatment of hernia, lysosomal disease, keloids, hypertrophic scars, muscular dystrophy or spinal cord injury.

It is sufficient that the kit contains a package comprising the pharmaceutical composition contained in a container, and a package insert or label explaining the use of the pharmaceutical composition for treatment of hernia, lysosomal disease, keloids, hypertrophic scars, muscular dystrophy or spinal cord injury. In other words, it may also contain other constituent components.

(3) Production Method

One aspect of the present invention relates to a method for producing a package comprising a pharmaceutical composition contained in a container, the production method including a first step of putting a solution containing not less than 2 μg and not more than 8 μg of a saccharide-degrading enzyme into a container, and a second step of lyophilizing the solution to obtain a pharmaceutical composition of a unit dose.

In the first step, although the solvent used for preparation of the solution containing the saccharide-degrading enzyme is not particularly restricted, for example, a buffer solution such as water, physiological saline or phosphate buffer may be used. The solution may also include a pharmaceutically acceptable carrier as mentioned above. Although the pH of the solution containing the saccharide-degrading enzyme contained in the container is not particularly restricted, it is preferably in the range of 6.5 or higher and 7.5 or lower.

In a preferred embodiment, the solution containing the saccharide-degrading enzyme is contained in the container in the first step such that the enzyme activity per container is not more than 4 units. In a more preferred embodiment, the solution is contained in the container such that the enzyme activity per container is not less than 0.5 units and not more than 4 units. In an even more preferred embodiment, the solution is contained in the container such that the enzyme activity per container is not less than 1 unit and not more than 3 units. In a particularly preferred embodiment, the solution is contained in the container such that the enzyme activity per container is not less than 1.25 units and not more than 2.5 units.

The second step includes a lyophilization step in which the solution containing the saccharide-degrading enzyme is frozen and the moisture is removed by sublimation while in a frozen state for drying. In the second step, drying is carried out until the water content of the pharmaceutical composition after lyophilization becomes not more than 5% (w/w), for example. The drying in the second step is preferably carried out until the water content of the pharmaceutical composition after lyophilization becomes not more than 3% (w/w), and more preferably the drying is carried out until the water content becomes not more than 2% (w/w).

The production method according to the present invention can directly employ the descriptions, examples, preferred ranges, etc., for the above-described "(1) composition and package" or the above-described "(2) kit."

As another mode, the present invention also includes the use of a unit dose formulation in production of a pharmaceutical composition to be used for treatment of hernia, lysosomal disease, keloids, hypertrophic scars, muscular dystrophy or spinal cord injury, which is the use of a unit dose formulation containing a lyophilized saccharide-degrading enzyme with a titer of not less than 0.3 unit/μg as an active ingredient, and containing the saccharide-degrading enzyme in an amount of not less than 2 μg and not more than 8 μg. Also, as another mode, the present invention also includes the use of a unit dose formulation for treatment of hernia, lysosomal disease, keloids, hypertrophic scars, muscular dystrophy or spinal cord injury, which is the use of a unit dose formulation containing a lyophilized saccharide-degrading enzyme with a titer of not less than 0.3 unit/μg as an active ingredient, and containing the saccharide-degrading enzyme in an amount of not less than 2 μg and not more than 8 μg. Further, as another mode, the present invention also includes a unit dose formulation to be used for treatment of hernia, lysosomal disease, keloids, hypertrophic scars, muscular dystrophy or spinal cord injury, which is the unit dose formulation containing a lyophilized saccharide-degrading enzyme with a titer of not less than 0.3 unit/μg as an active ingredient, and containing the saccharide-degrading enzyme in an amount of not less than 2 μg and not more than 8 μg.

Exemplary embodiments of the present invention will now be described, with the understanding that the present invention is not limited by these embodiments.

<1>
A pharmaceutical composition comprising a lyophilized saccharide-degrading enzyme having a titer of not less than 0.3 unit/μg as an active ingredient, and
the pharmaceutical composition being a unit dose formulation in which an amount of the saccharide-degrading enzyme is not less than 2 μg and not more than 8 μg.
<2> The pharmaceutical composition according to <1>, wherein the enzyme activity is not more than 4 units.
<3> The pharmaceutical composition according to <1> or <2>, wherein the enzyme activity of the saccharide-degrading enzyme is not less than 75%, where 100% is defined as the value before lyophilization.
<4> The pharmaceutical composition according to any one of <1> to <3>, wherein the composition has a storage stability for the duration of not less than 12 months at 5° C.±3° C.
<5> The pharmaceutical composition according to any one of <1> to <4>, wherein the saccharide-degrading enzyme is a glycosaminoglycan degrading enzyme.
<6> The pharmaceutical composition according to <5>, wherein the glycosaminoglycan degrading enzyme is a chondroitinase.
<7> The pharmaceutical composition according to <6>, wherein the chondroitinase is chondroitinase ABC.
<8> The pharmaceutical composition according to any one of <1> to <7>, wherein the pharmaceutical composition includes a pharmaceutically acceptable carrier.
<9> The pharmaceutical composition according to <8>, wherein the carrier includes at least either of polyalkylene glycol and sucrose.
<10> The pharmaceutical composition according to any one of <1> to <9>, wherein the pharmaceutical composition is for treatment of herniation, lysosomal disease, keloids, hypertrophic scars, muscular dystrophy or spinal cord injury.
<11> A package comprising the pharmaceutical composition according to any one of <1> to <10> contained in a container.
<12> The package according to <11>, wherein the container is a vial, syringe or ampule.
<13> A kit containing a package comprising the pharmaceutical composition according to any one of <1> to <10> contained in a container, and a package insert or label explaining the use of the pharmaceutical composition for treatment of hernia, lysosomal disease, keloids, hypertrophic scars, muscular dystrophy or spinal cord injury.
<14>
A method for producing a package comprising a container containing a pharmaceutical composition, the method comprising:
  a step of putting a solution comprising not less than 2 μg and not more than 8 μg of a saccharide-degrading enzyme into the container, and
  a step of lyophilizing the solution so that a unit dose of the pharmaceutical composition can be provided.
<15> The method for producing according to <14>, wherein the pharmaceutical composition comprises the saccharide-degrading enzyme having a titer of not less than 0.3 unit/μg.
<16> The method for producing according to <14> or <15>, wherein an enzyme activity of the solution contained in the container is not more than 4 units.
<17> The method for producing according to any one of <14> to <16>, wherein the enzyme activity of the saccharide-degrading enzyme after lyophilization is not less than 75%, where 100% is defined as the enzyme activity before lyophilization.
<18> The method for producing according to any one of <14> to <17>, wherein the saccharide-degrading enzyme is a glycosaminoglycan degrading enzyme.
<19> The production method for producing according to <18>, wherein the glycosaminoglycan degrading enzyme is a chondroitinase.
<20> The method for producing according to <19>, wherein the chondroitinase is chondroitinase ABC.
<21> The method for producing according to any one of <14> to <20>, wherein the pharmaceutical composition includes a pharmaceutically acceptable carrier.
<22> The method for producing according to <21>, wherein the carrier includes at least either of polyalkylene glycol and sucrose.
<23> The method for producing according to any one of <14> to <22>, wherein the pharmaceutical composition is for treatment of hernia, lysosomal disease, keloids, hypertrophic scars, muscular dystrophy or spinal cord injury.
<24> The method for producing according to any one of <14> to <23>, wherein the container is a vial, syringe or ampule.

EXAMPLES

The present invention will now be described in greater detail. However, this description is not intended to restrict the technical scope of the present invention.

Preparation Example

1) Preparation of Chondroitinase ABC

Chondroitinase ABC was prepared according to the method described in Japanese Published Unexamined Patent Application No. H6-153947. That is, it was produced by purification from a *Proteus vulgaris* culture supernatant. The titer of the obtained chondroitinase ABC was 0.4 U/µg.

2) Enzyme Activity Measurement and Concentration Measurement of Chondroitinase ABC The enzyme activity of the chondroitinase ABC was measured by the following method.

The enzyme sample (chondroitinase ABC) was diluted 4000-times with 0.01% (w/v) casein reagent (20 mM phosphate buffer). To 100 µL of the diluted enzyme sample, 400 µL of substrate solution (3 mg/ml sodium chondroitin sulfate (Japanese Pharmaceutical Codex), 50 mM 2-amino-2-hydroxymethyl-1,3-propanediol, 50 mM sodium acetate, pH 8) was added and mixed. After reacting the solution at 37° C. for 20 minutes, it was heated for 1 minute in a water bath at 100° C. The reaction mixture was cooled to room temperature, and 5.0 mL of 0.05 M hydrochloric acid was added to prepare a sample solution. Standard chondroitinase ABC was diluted 400-times with 0.01% (w/v) casein reagent. The same procedure for preparation of the sample solution was carried out with 100 µL of the diluted standard chondroitinase ABC solution, to prepare a standard solution. The same procedure for preparation of the sample solution was also carried out for 100 µL of 0.01% (w/v) casein reagent, to prepare a control solution. The absorbance $A_T$, $A_s$ and $A_B$ at a wavelength of 232 nm were measured for the sample solution, standard solution and control solution, using ultraviolet-visible spectrophotometry, and the enzyme solution activity (U/mL) of each was determined by the following formula. Here, the enzyme solution activity is the enzyme activity per unit liquid volume.

Enzyme solution activity $(U/mL) = (A_T - A_B)/(A_s - A_B) \times 4000/400 \times Us$ $A_T$: Absorbance of sample solution
$A_B$: Absorbance of control solution
$A_s$: Absorbance of standard solution
Us: Enzyme solution activity of standard chondroitinase ABC (U/mL)

1 U (unit) was defined as the value of enzyme activity that catalyzes reaction to free 1 micromole of unsaturated disaccharide in 1 minute, under the reaction conditions specified above. The values for the enzyme activity used herein were determined based on the enzyme solution activity.

The amount of chondroitinase ABC enzyme (protein, µg) was measured by following Lowry method. That is, 2.5 mL of alkaline copper reagent was added to and mixed with 0.5 mL of the enzyme sample (chondroitinase ABC) diluted 50-times with pure water, and the mixture was allowed to stand for 10 minutes at room temperature (20° C. or higher and 25° C. or lower). Next, 0.25 mL of 1 mol/L phenol reagent was added to the liquid and allowed to stand for 30 minutes at room temperature to prepare a sample solution. Bovine serum albumin was dissolved in water to prepare a solution to a concentration of 30 µg/mL, 40 µg/mL, 50 µg/mL, 60 µg/mL or 70 µg/mL, and the same procedure for the 50-times diluted enzyme sample was carried out for 0.5 mL of each solution to prepare a standard solution. The same procedure for the 50-times diluted enzyme sample was also carried out for 0.5 mL of water, to prepare a blank solution. The absorbance of each solution at a wavelength of 750 nm was measured. The absorbance and protein concentration of the standard solution was plotted by a linear regression method, to determine a standard curve most closely approximating each point. The amount of protein in each sample solution was determined from the obtained standard curve and the absorbance of the sample solution.

3) Preparation of Buffer for Enzyme Solution

A buffer for enzyme solution was prepared so as to have the following composition.

(Composition; per 1 L of distilled water for injection)
Sodium hydrogenphosphate hydrate(disodium hydrogenphosphate): 1.125 mg
sodium dihydogen phosphate: 0.3 mg
Sucrose: 5 mg
Polyethylene glycol 3350: 10 mg
pH: 6.5 or higher and 7.5 or lower Test Example 1

Chondroitinase ABC solution prepared using the buffer for enzyme solution was filled into 3 ml glass vials (product of Schott AG), to the following enzyme amounts.

Sample 1: 1.3 µg/vial (0.5 U/vial)
Sample 2: 2.5 µg/vial (1.00 U/vial)
Sample 3: 5.0 µg/vial (2.00 U/vial)
Sample 4: 9.1 µg/vial (3.63 U/vial)

The enzyme solution contained in each vial was lyophilized (to a water content of not more than 2% (w/w)) under the following conditions. After lyophilization, the pressure inside the vial was recovered with nitrogen gas and sealed with a rubber stopper to obtain a unit dose formulation.

(Lyophilization Conditions)

Step 1: The temperature was cooled from room temperature to minus 35° C. under ordinary pressure to freeze the sample.

Step 2: The state of minus 35° C. temperature, ordinary pressure was maintained for 30 minutes.

Step 3: The state of minus 35° C. temperature, 13.3 Pa vacuum was maintained for 5 hours.

Step 4: While maintaining a vacuum of 13.3 Pa, the temperature was raised from minus 35° C. to 25° C.

Step 5: The state of 25° C. temperature, 13.3 Pa vacuum was maintained for 5 hours.

Each vial was measured for enzyme activity (U/unit dose) after lyophilization. The titer (U/µg) and relative enzyme activity (the enzyme activity after lyophilization, where 100% was defined as the enzyme activity before lyophilization) (%) were also calculated. The results are shown in Table 1.

TABLE 1

|  | Sample 1 | Sample 2 | Sample 3 | Sample 4 |
|---|---|---|---|---|
| Enzyme amount (µg/unit dose) | 1.3 | 2.5 | 5.0 | 9.1 |
| Enzyme activity before lyophilization (U/unit dose) | 0.50 | 1.00 | 2.00 | 3.63 |
| Enzyme activity after lyophilization (U/unit dose) | 0.43 | 0.94 | 1.96 | 3.13 |

TABLE 1-continued

|  | Sample 1 | Sample 2 | Sample 3 | Sample 4 |
|---|---|---|---|---|
| Titer after lyophilization (U/μg) | 0.331 | 0.376 | 0.392 | 0.344 |
| Relative enzyme activity (%) | 86.0 | 94.0 | 98.0 | 86.3 |
| Remarks | Comparative Example | Example | Example | Comparative Example |

The results in Table 1 demonstrate that, by limiting the amount of saccharide-degrading enzyme per unit dose to a specific range (not less than 2.0 μg and not more than 8.0 μg), it was possible to provide a lyophilized preparation with very high titer.

Test Example 2

The buffer for enzyme solution was used to prepare a chondroitinase ABC solution. The prepared enzyme solution was put into a glass vial in the same manner as Test Example 1, such that the amount of enzyme was 1.5 U/vial, and lyophilized (to a water content of not more than 2% (w/w)). After lyophilization, the pressure inside the vial was recovered with nitrogen gas and sealed with a rubber stopper to obtain a unit dose formulation.

Each obtained unit dose formulation was measured for enzyme activity (U/vial) after lyophilization. As a result, enzyme activity of 1.5 U/vial was maintained even after lyophilization.

Test Example 3

A unit dose formulation (1.5 U/vial) was obtained according to the method of Test Example 1. The obtained unit dose formulation was stored under the following conditions 1 or 2. The titer of the enzyme after each storage period was determined.
Conditions 1): 25° C.±2° C., light-resistant
Conditions 2): 5° C.±3° C., light-resistant As a result, under conditions 1, the titer retention rate for 1 month, 3 months and 6 months after the start of storage was not less than 95% with respect to 100% as the titer at the start of storage. Under conditions 2, the titer retention rate for 3 months, 6 months, 12 months, 24 months and 36 months after the start of storage was not less than 95% with respect to 100% as the titer at the start of storage.

Although the present invention has been described in relation to specific examples and various embodiments, it will be readily appreciated by a person skilled in the art that numerous modifications and applications of the embodiments described herein are possible without departing from the spirit and scope of the present invention.

All literatures, patent applications, and technical standards described herein are incorporated herein by reference to the same extent as if individual literatures, patent applications, and technical standards are specifically and individually indicated to be incorporated by reference.

The invention claimed is:

1. A method for producing a package comprising a pharmaceutical composition, the method comprising:
   putting a solution comprising not less than 2.5 μg and not more than 5 μg of a saccharide-degrading enzyme into a container; and
   lyophilizing the solution to obtain a unit dose of the pharmaceutical composition,
   wherein the saccharide-degrading enzyme is chondroitinase ABC,
   wherein a water content of the pharmaceutical composition is not more than 2% (w/w), and
   wherein the pharmaceutical composition comprises the saccharide-degrading enzyme having a titer of not less than 0.34 unit/μg.

2. The method according to claim 1, wherein the package encapsulates an inert gas or is deaerated.

3. The method according to claim 1, wherein the chondroitinase ABC is derived from *Proteus vulgaris*.

4. The method according to claim 1, wherein a pH of the solution containing the saccharide-degrading enzyme put into the container is in a range of 6.5 to 7.5.

5. The method according to claim 1, wherein the pharmaceutical composition further comprises at least one selected from the group consisting of sucrose, polyethylene glycol, and a buffering agent.

6. The method according to claim 5, wherein the pharmaceutical composition comprises sucrose, polyethylene glycol, and the buffering agent.

7. The method according to claim 6, wherein the polyethylene glycol has an average molecular weight of not less than 2000 and not more than 9000.

8. The method according to claim 1, further comprising obtaining a culture of microbes or animal cells that produce the saccharide-degrading enzyme and collecting the saccharide-degrading enzyme from the cultured product.

9. The method according to claim 1, wherein the pharmaceutical composition comprises the saccharide-degrading enzyme having a titer of not less than 0.34 unit/μg and not more than 0.5 unit/μg.

10. A method for producing a package comprising a pharmaceutical composition, the method comprising:
    putting a solution comprising not less than 2.5 μg and not more than 5 μg of a saccharide-degrading enzyme into a container; and
    lyophilizing the solution to obtain a unit dose of the pharmaceutical composition,
    wherein:
    the saccharide-degrading enzyme is chondroitinase ABC,
    a water content of the pharmaceutical composition is not more than 2% (w/w),
    the pharmaceutical composition comprises the saccharide-degrading enzyme having a titer of not less than 0.34 unit/μg and not more than 0.5 unit/μg, and
    the package encapsulates an inert gas or is deaerated.

11. The method according to claim 10, wherein the chondroitinase ABC is derived from *Proteus vulgaris*.

12. The method according to claim 10, wherein a pH of the solution containing the saccharide-degrading enzyme put into the container is in a range of 6.5 to 7.5.

13. The method according to claim 10, wherein the pharmaceutical composition further comprises at least one selected from the group consisting of sucrose, polyethylene glycol, and a buffering agent.

14. The method according to claim 10, wherein the pharmaceutical composition further comprises sucrose, polyethylene glycol, and a buffering agent.

15. The method according to claim 10, wherein the polyethylene glycol has an average molecular weight of not less than 2000 and not more than 9000.

16. The method according to claim 10, further comprising:
   obtaining a culture of microbes or animal cells that produce the saccharide-degrading enzyme, and
   collecting the saccharide-degrading enzyme from the cultured product.

17. A method for producing a package comprising a pharmaceutical composition, the method comprising:
   putting a solution comprising not less than 2.5 µg and not more than 5 µg of a saccharide-degrading enzyme into a container; and
   lyophilizing the solution to obtain a unit dose of the pharmaceutical composition,
   wherein:
      the saccharide-degrading enzyme is chondroitinase ABC derived from *Proteus vulgaris*,
      a water content of the pharmaceutical composition is not more than 2% (w/w),
      the pharmaceutical composition comprises the saccharide-degrading enzyme having a titer of not less than 0.34 unit/µg and not more than 0.5 unit/µg,
      the package encapsulates an inert gas or is deaerated,
      a pH of the solution containing the saccharide-degrading enzyme put into the container is in a range 6.5 to 7.5,
      the pharmaceutical composition comprises sucrose, polyethylene glycol, and a buffering agent, and
      the polyethylene glycol has an average molecular weight of not less than 2000 and not more than 9000.

* * * * *